(12) United States Patent
Gilmartin

(10) Patent No.: US 12,336,967 B2
(45) Date of Patent: Jun. 24, 2025

(54) BUTYRIC ACID BASED ASPIRATION DETECTION AND NASOGASTRIC OR INTUBATION PLACEMENT VERIFICATION PLATFORMS AND METHODS

(71) Applicant: Charles Kim Gilmartin, San Anselmo, CA (US)

(72) Inventor: Charles Kim Gilmartin, San Anselmo, CA (US)

( * ) Notice: Subject to any disclaimer, the term of this patent is extended or adjusted under 35 U.S.C. 154(b) by 1010 days.

(21) Appl. No.: 17/353,187

(22) Filed: Jun. 21, 2021

(65) Prior Publication Data

US 2021/0322279 A1    Oct. 21, 2021

Related U.S. Application Data

(63) Continuation-in-part of application No. 17/195,591, filed on Mar. 8, 2021, and a continuation-in-part of
(Continued)

(51) Int. Cl.
*A61M 16/04* (2006.01)
*A61J 15/00* (2006.01)
(Continued)

(52) U.S. Cl.
CPC ...... *A61J 15/0084* (2015.05); *A61M 16/0003* (2014.02); *A61M 16/0402* (2014.02);
(Continued)

(58) Field of Classification Search
None
See application file for complete search history.

(56) References Cited

U.S. PATENT DOCUMENTS

| 4,090,518 A | * | 5/1978 | Elam | A61M 16/0484 |
| | | | | 128/207.15 |
| 4,351,330 A | * | 9/1982 | Scarberry | A61N 1/0517 |
| | | | | 607/124 |

(Continued)

OTHER PUBLICATIONS

DiBardina DM, Wunderrink RG (Feb. 2015) "Aspiration Pneumonia: A Review of Modern Trends." Journal of Critical Care. 30 (1): 40-48.

(Continued)

*Primary Examiner* — LaToya M Louis
(74) *Attorney, Agent, or Firm* — Blynn L. Shideler; Krisanne Shideler; BLK Law Group

(57) ABSTRACT

A butyric acid detection based platform for verifying placement of a patient airway device or a gastric tube comprising at least one of i) a colorimetric based butyric acid detection platform, ii) a bioelectronic sensors based butyric acid detection platform using olfactory receptors, and iii) an IR based butyric acid detection platform. Each platform comprises a housing coupled to the patient airway device or gastric tube whereby flow from the coupled patient airway device or a gastric tube can flow through an internal passage of the housing; and wherein sensors within the housing come into contact with the flow from the coupled patient airway device or a gastric tube, the sensors including at least one of a chemical sensor array including at least one of i) colorimetric based butyric acid sensor, ii) a bioelectronic butyric acid detection sensor using olfactory receptors, and iii) an IR based butyric acid sensor.

9 Claims, 8 Drawing Sheets

Related U.S. Application Data application No. 17/088,794, filed on Nov. 4, 2020, application No. 17/353,187 is a continuation-in-part of application No. PCT/US2021/022438, filed on Mar. 15, 2021.

(60) Provisional application No. 63/041,998, filed on Jun. 21, 2020, provisional application No. 62/986,630, filed on Mar. 7, 2020, provisional application No. 62/930,096, filed on Nov. 4, 2019, provisional application No. 62/988,925, filed on Mar. 13, 2020.

(51) Int. Cl.
*A61M 16/00* (2006.01)
*A61M 16/06* (2006.01)
*A61M 16/08* (2006.01)

(52) U.S. Cl.
CPC .... *A61M 16/0666* (2013.01); *A61M 16/0816* (2013.01); *A61J 2200/70* (2013.01); *A61M 2205/13* (2013.01); *A61M 2205/3303* (2013.01); *A61M 2205/3313* (2013.01); *A61M 2205/6081* (2013.01)

(56) References Cited

U.S. PATENT DOCUMENTS

| | | | | |
|---|---|---|---|---|
| 4,774,945 | A * | 10/1988 | White | A61M 16/04 128/207.18 |
| 4,821,710 | A * | 4/1989 | Greunwald | A61M 16/0488 128/207.14 |
| 7,178,519 | B2 * | 2/2007 | Melker | A61M 16/0488 128/207.14 |
| 7,747,319 | B2 * | 6/2010 | Freeman | A61H 31/005 128/207.14 |
| 7,921,847 | B2 * | 4/2011 | Totz | A61M 16/0488 128/207.14 |
| 8,720,445 | B2 * | 5/2014 | Cain | A61M 16/04 128/207.14 |
| 8,740,768 | B2 * | 6/2014 | Lior | A61F 5/0059 600/37 |
| 10,940,282 | B2 * | 3/2021 | Pacey | A61M 16/208 |
| 11,077,029 | B2 * | 8/2021 | Elia | A61B 5/4836 |
| 11,172,876 | B2 * | 11/2021 | Gilmartin | A61B 5/082 |
| 11,304,877 | B2 * | 4/2022 | Strawder | A61B 5/4238 |
| 2007/0017527 | A1 * | 1/2007 | Totz | A61M 16/0486 128/207.15 |
| 2007/0163596 | A1 * | 7/2007 | Mikkaichi | A61M 16/0493 128/207.14 |
| 2010/0106208 | A1 * | 4/2010 | Freeman | A61H 31/005 607/5 |
| 2010/0179417 | A1 * | 7/2010 | Russo | A61M 39/08 604/264 |
| 2012/0204866 | A1 * | 8/2012 | Kizer | A61M 25/0102 128/200.26 |
| 2013/0150689 | A1 * | 6/2013 | Shaw-Klein | A61B 5/6812 204/403.14 |
| 2014/0137867 | A1 * | 5/2014 | Pacey | A61M 16/0488 128/207.14 |
| 2014/0275716 | A1 * | 9/2014 | Connor | A61N 1/36057 600/9 |
| 2014/0333007 | A1 * | 11/2014 | Nasir | A61M 16/0415 128/207.15 |
| 2016/0081831 | A1 * | 3/2016 | Chen | A61F 5/0033 606/192 |
| 2017/0146970 | A1 * | 5/2017 | Joo | G05B 19/042 |
| 2019/0167171 | A1 * | 6/2019 | Gallagher | A61J 15/008 |
| 2019/0240115 | A1 * | 8/2019 | Elia | A61M 1/73 |
| 2019/0282160 | A1 * | 9/2019 | Gilmartin | A61B 5/742 |
| 2020/0237202 | A9 * | 7/2020 | Shields | A61B 1/07 |
| 2020/0305999 | A1 * | 10/2020 | Szoka | A61B 1/00066 |
| 2020/0330324 | A1 * | 10/2020 | Freeman | A61N 1/3925 |
| 2021/0346626 | A1 * | 11/2021 | Pacey | A61M 16/0488 |
| 2021/0353505 | A1 * | 11/2021 | Elia | A61M 1/73 |
| 2021/0386949 | A1 * | 12/2021 | Pacey | A61M 16/0057 |

OTHER PUBLICATIONS

Lanspa M, Peyrani P, Wiemkwn T, Wilson E, Ramirez J, Dean N (2015), "Characteristics associated with clinician diagnosis of aspiration pneumonia; a descriptive study of afflicted patients and their outcomes". J Hosp Med. 10 (2): 90-6.

Van Der Maarel-Wierink CD, Vanobbergen JN, Bronkhorst EM, Schols JM, De Baat C. "Meta-analysis of dysphagia and aspiration pneumonia in frail elders" J Dent Res 2011;90:1398-404.

Ilya Kagan, Moran Hellerman-Itzhaki, Ido Neuman, Yehuda D. Glass, Pierre Singer"Reflux events detected by multichannel bioimpedance smart feeding tube during high flow nasal cannula oxygen therapy and enteral feeding: First case report" Journal of Critical Care vol. 60, Dec. 2020, pp. 226-229.

Katz, SH; Falk, JL (2001). "Misplaced endotracheal tubes by paramedics in an urban emergency medical services system" (PDF). Ann Emerg Med. 37 (1): 32-7.

Jones, JH; Murphy, MP; Dickson, RL; Somerville GG; Brizendine, EJ (2004) "Emergency Physician Verified Out-of-Hospital Intubation: Miss Rates by Paramedics" Academic Emergency Medicine, 11(6): 707-9.

Abstract of: Fein AMm, "Pneumonia in the elderly. Special diagnostic and therapeutic considerations" Med Clin North Am 1994, 78:1015-33.

Abstract of: Oh E, Weintraub N, Dhanani S. "Can we prevent aspiration pneumonia in the nursing home?" J Am Med Dir Assoc 2005;6 (3 Suppl):S76-80.

Abstract of: Shea SR, MacDonald JR, Gruzinski G: "Prehospital endotracheal tube airway or esophageal gastric tube airway: A critical comparison" Ann Emerg Med 1985; 14:102-112.

* cited by examiner

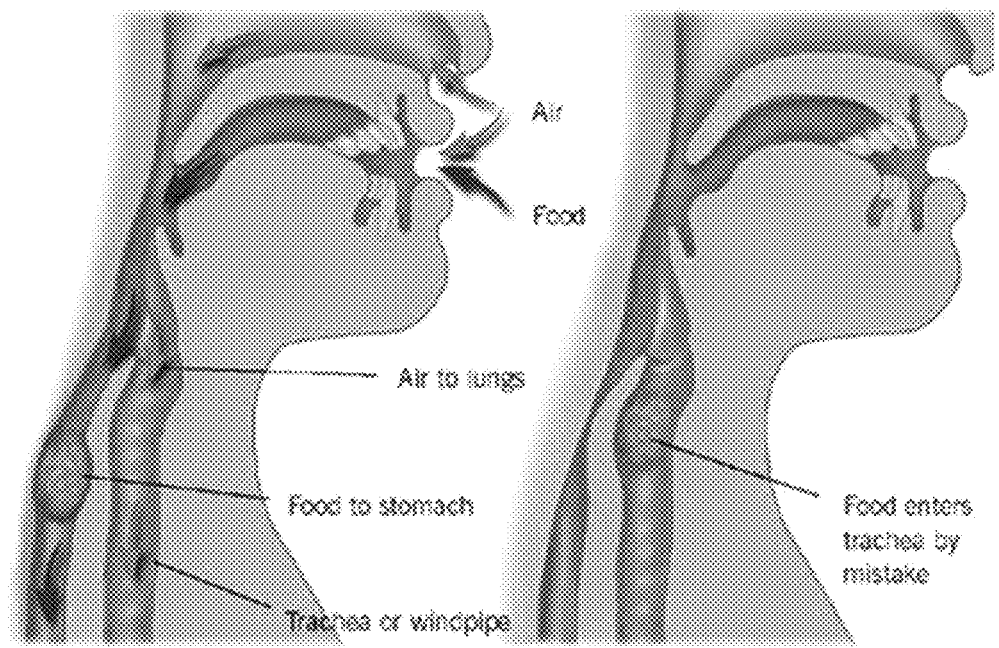
PRIOR ART
FIG. 1A
PRIOR ART
FIG. 1B
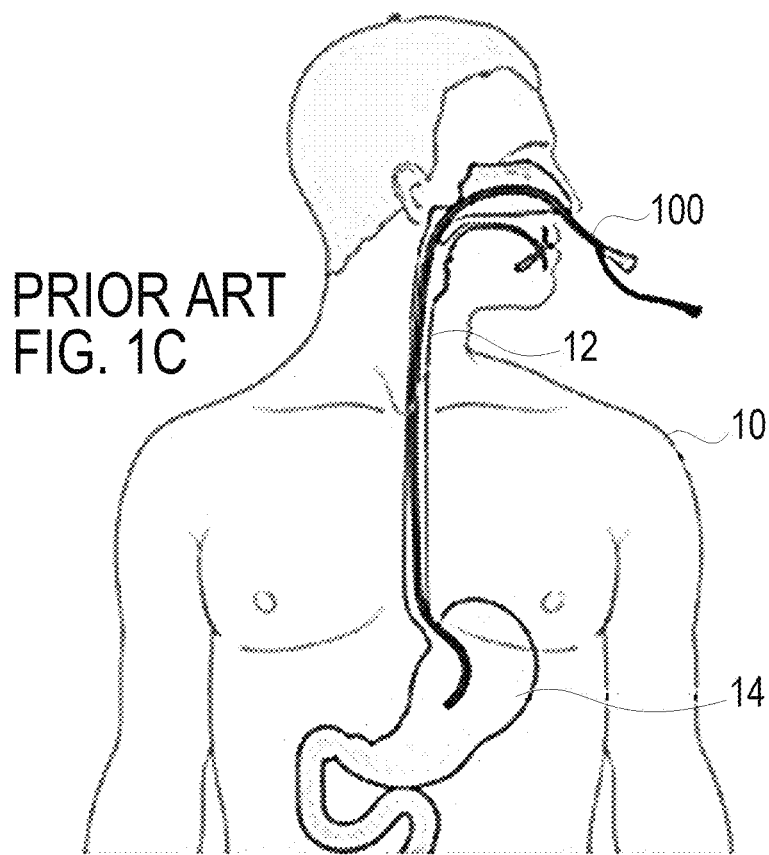
PRIOR ART
FIG. 1C

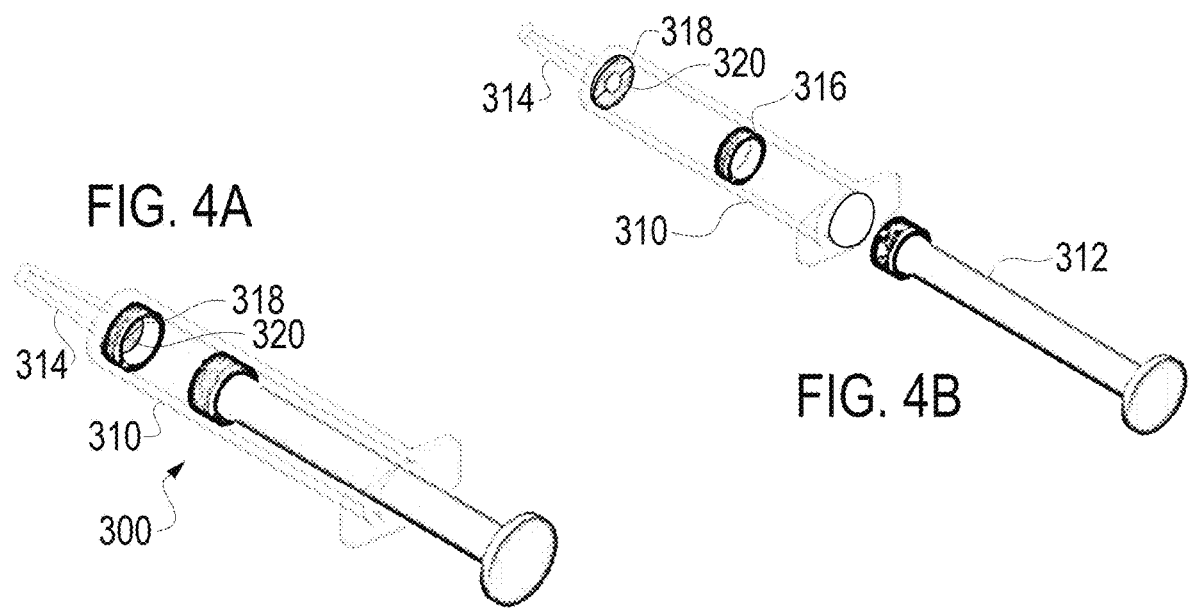
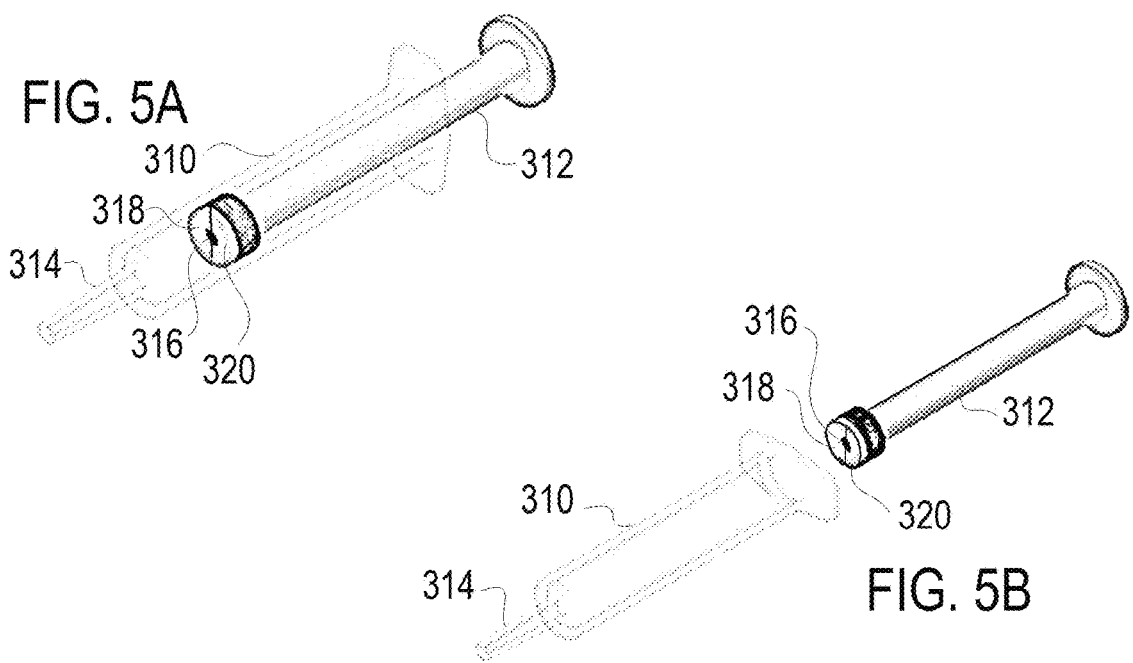

BUTYRIC ACID BASED ASPIRATION DETECTION AND NASOGASTRIC OR INTUBATION PLACEMENT VERIFICATION PLATFORMS AND METHODS

RELATED APPLICATIONS

This application is a continuation in part of U.S. patent application Ser. No. 17/195,591 filed Mar. 8, 2021 titled "Integrated Multimodal Aspiration Detection and Intubation Placement Verification System and Method" which application is incorporated herein in its entirety.

U.S. patent application Ser. No. 17/195,591 claims priority to U.S. Patent Application Ser. No. 62/986,630 filed Mar. 7, 2020 titled "Gas and Bioelectronic analysis/detection of compounds of emesis to facilitate early detection and/or prevention of aspiration and confirmation of correct placement of advanced airway equipment" which application is incorporated herein in its entirety.

U.S. patent application Ser. No. 17/195,591 is a continuation in part of U.S. patent application Ser. No. 17/088,794 Filed Nov. 4, 2020 titled "Integrated Multimodal Colormetric Based Aspiration Detection and Intubation Placement Verification System and Method" which application is incorporated herein in its entirety.

U.S. patent application Ser. No. 17/088,794 claims priority to U.S. Patent Application Ser. No. 62/930,096 filed Nov. 4, 2019 titled "Integrated Multimodal Colormetric Based Aspiration Detection and Intubation Placement Verification System and Method" which application is incorporated herein in its entirety.

This application is a continuation in part of International Patent Application Serial Number PCT/US21/22438 filed Mar. 15, 2021 titled "Integrated Multimodal Aspiration Detection and Intubation Placement Verification System and Method" which application is incorporated herein in its entirety.

International Patent Application Serial Number PCT/US21/22438 claims priority to U.S. Patent Application Ser. No. 62/988,925 filed Mar. 13, 2020 titled "COLORIMETRIC PAPER BASED CONFIRMANTION OF PROPER PLACEMENT OF OROGASTRIC/NASOGASTRIC AND FEEDING TUBES" which application is incorporated herein in its entirety.

This application claims priority to U.S. Patent Application Ser. No. 63/041,998 filed Jun. 21, 2020 titled "BIOELECTRIC/OLFACTORY/DIGITAL OLFACTION CONFIRMATION OF PROPER PLACEMENT OF OROGASTRIC/NASOGASTRIC and FEEDING TUBES" which application is incorporated herein in its entirety.

BACKGROUND INFORMATION

1. Field of the Invention

The present invention relates to improving respiratory monitory procedures and placement of orogastric/nasogastric or feeding tubes, and more broadly to a buteric acid detection based method and an apparatus for aspiration detection in respiratory assist device patients and for intubation verification of endotracheal tubes or other airway devices (e.g. laryngeal mask airways) and placement verification of orogastric or nasogastric tubes.

2. Background Information

Respiratory Devices

Aspiration is generally defined as the entry of foreign material into the lungs. This can be due to inhalation of food or liquids during swallowing or due to regurgitation of stomach contents. Aspiration is schematically shown in Prior Art FIG. 1B, while FIG. 1A illustrates conventional swallowing.

Patient aspiration can lead to a number of patient complications including aspiration pneumonia and aspiration pneumonitis.

Studies have put incidence rates of aspiration pneumonia at around 5 to 15% of Community Acquired Pneumonia. See, for reference, Dibardina D M, Wunderrink R G (February 2015) "Aspiration Pneumonia: A Review of Modern Trends." *Journal of Critical Care*. 30 (1): 40-48; See also Marik P E. "Aspiration pneumonitis and aspiration pneumonia" *N Engl J Med* 2001; 344:665-71. The rate of aspirational pneumonia can be as high as 20% in nursing home acquired pneumonia, see for reference Oh E, Weintraub N, Dhanani S. "Can we prevent aspiration pneumonia in the nursing home?" *J Am Med Dir Assoc* 2005; 6 (3 Suppl):S76-80, and Fein A M, "Pneumonia in the elderly. Special diagnostic and therapeutic considerations" Med Clin North Am 1994, 78:1015-33.

Additionally, it has been estimated that aspiration pneumonia occurs in 1 in every 2-3000 patients undergoing surgery, and this rate can be 3× higher in patients undergoing thoracic surgery. It occurs frequently in patients admitted with drug overdose and exhibits higher mortality rates. See Lanspa M, Peyrani P, Wiemkwn T, Wilson E, Ramirez J, Dean N (2015), "Characteristics associated with clinician diagnosis of aspiration pneumonia; a descriptive study of afflicted patients and their outcomes". *J Hosp Med*. 10 (2): 90-6. It is the most common cause of death in patients suffering from dysphagia due to neurologic disorders, see van der Maarel-Wierink C D, Vanobbergen J N, Bronkhorst E M, Schols J M, de Baat C. "Meta-analysis of dysphagia and aspiration pneumonia in frail elders" *J Dent Res* 2011; 90:1398-404.

As alluded to above, aspiration is more common or becomes more likely with a number of conditions. For example, aspiration is more likely in the following conditions, including: difficulty swallowing (certain neurological conditions, stroke, etc.); vomiting, GERD, Placement and use of an NG tube, alcoholism, impaired consciousness, impaired cognition, seizures, use of a ventilator. See also a recent, at the time of this filing, paper by IlyaKagan, Moran Hellerman-ltzhaki, Ido Neuman, Yehuda D. Glass, Pierre Singer titled "Reflux events detected by multichannel bio-impedance smart feeding tube during high flow nasal cannula oxygen therapy and enteral feeding: First case report" Journal of Critical Care Volume 60, December 2020, Pages 226-229.

A separate complication of aspiration is aspiration pneumonitis, wherein the inhaled substances during aspiration are directly toxic to the lungs, causing chemical pneumonitis, also called Mendelson syndrome. Gastric acid, with a low pH (1.5-3.0), can cause corrosive damage to the lungs. Pneumonitis can resolve within a few days, or progress to Acute Respiratory Distress Syndrome (ARDS). There can also be a superimposed (aka secondary) bacterial infection in the tissue damaged by chemical pneumonitis. Aspiration pneumonitis is distinctly different from aspiration pneumonia. Aspiration pneumonitis (Mendelson's syndrome) is a chemical injury caused by the inhalation of sterile gastric contents, whereas aspiration pneumonia is an infectious process caused by the inhalation of oropharyngeal secretions that are colonized by pathogenic bacteria. Aspiration pneumonia presents with many of the same symptoms and signs as pneumonitis, but takes longer to develop. Fever caused by aspiration pneumonia is generally of a higher grade than in pneumonitis.

The applicant has been developing tools to minimize aspiration that can lead to the above complications. The applicant has developed a method of aspiration detection in respiratory assist device patients comprising the steps of: coupling an HCL sensor to one of a respiratory assist device of a patient; detecting the presence of HCL particles indicative of aspiration of the patient via a processer coupled to the HCL sensor; and displaying results for aspiration of the patient on the audio visual display. This earlier HCL sensor platform did have proposed applications in a variety of respiratory assist devices including in the nasal cannula and masks of ventilation systems and also in CPAP devices, Bipap devices and endotracheal tubes. The present invention represents continuation of this work, and can be considered an Butyric acid detection based platform in this same family.

An endotracheal tube is a specific type of tracheal tube that is nearly always inserted through the mouth (orotracheal) or nose (nasotracheal), and is a catheter that is inserted into the trachea for the primary purpose of establishing and maintaining a patient airway and to ensure the adequate exchange of oxygen and carbon dioxide. Tracheal intubation, usually simply referred to as intubaton, is the placement of a flexible catheter, e.g. plastic tube, into the trachea (windpipe) to maintain an open airway (or sometimes to serve as a conduit through which to administer certain drugs). It is frequently performed in critically injured, ill, or anesthetized patients to facilitate ventilation of the lungs, including mechanical ventilation, and to prevent the possibility of asphyxiation or airway obstruction.

Endotracheal tubes used for intubation can often be inserted incorrectly, particularly in traumatic scenarios. See Katz, S H; Falk, J L (2001). "Misplaced endotracheal tubes by paramedics in an urban emergency medical services system" (PDF). *Ann Emerg Med.* 37 (1): 32-7. See also Jones, J H; Murphy, M P; Dickson, R L; Somerville G G; Brizendine, E J (2004) "Emergency Physician Verified Out-of-Hospital Intubation: Miss Rates by Paramedics" *Academic Emergency Medicine,* 11(6): 707-9. In the prehospital setting, the incidence of unrecognized esophageal intubation has been reported to be as high as 1.8-2.0%, see Shea S R, MacDonald J R, Gruzinski G: "Prehospital endotracheal tube airway or esophageal gastric tube airway: A critical comparison" Ann Emerg Med 1985; 14:102-112.

There is a significant need for validation of proper endotracheal intubation. The position of the American College of Emergency Physicians, revised in 2016, states that confirmation of proper endotracheal tube placement should be completed in all patients at the time of initial intubation both in the hospital and out-of-hospital settings. Physical examination methods such as auscultation of chest and epigastrium, visualization of thoracic movement, and fogging in the tube are deemed not sufficiently reliable to confirm endotracheal tube placement. Similarly, pulse oximetry and chest radiography are not reliable as sole techniques to determine endotracheal tube location.

During intubation, direct visualization of the endotracheal tube passing through the vocal cords into the trachea, especially with the use of a video-laryngoscope, has been deemed to constitute firm evidence of correct tube placement, but additional techniques should be used as objective findings to confirm proper endotracheal tube position. The use of an end-tidal carbon dioxide detector (i.e., continuous waveform capnography, colorimetric and non-waveform capnography) has been proposed to evaluate and confirm endotracheal tube position in patients who have adequate tissue perfusion. However existing esophageal detector devices are deemed not as reliable as the various forms of capnography for the verification of endotracheal tube placement. Further, for patients in cardiac arrest and for those with markedly decreased perfusion, both continuous and non-waveform capnography may be less accurate. In these situations, if capnography is inconclusive, other methods of confirmation are desirable.

Ultrasound imaging may be used to reliably confirm endotracheal tube placement. However, this must be performed by someone who is experienced in this technique, and is not a practical real time solution in most applications. For background see Birmingham P K, Cheney F W, Ward R J: Esophageal intubation: A review of detection techniques. Anesth Analg 1986; 65:886-91; and Standards for Basic Anesthetic Monitoring, American Society of Anesthesiologists (last amended October 23), Directory of Members, 1996; 1998:438-9.

There remains a need for a simple effective, efficient method and an apparatus for aspiration detection in respiratory assist device patients and for intubation verification of endotracheal tubes and other airway devices which can yield a reduction of morbidity and mortality of patients.

Gastric Tube

A conventional gastric tube 100 in a patient 10 is shown in FIG. 1C for reference. Gastric tubes 100 as a class typically include oro-gastric, nasogastric and feeding tubes and are typically formed of polyurethane, rubber or silicone. Sizes typically range from 4Fr (1.3 mm) common in pediatric patients to 18 Fr (6 mm) typical in adults. Gastric tubes 100 are ubiquitous and are used routinely in hospitals, outpatient surgery centers or clinics, long term care facilities, hospice and other various locations. Gastric tubes 100 are small tubes placed either through the nose (nasogastric) or mouth (oro-gastric) through the esophagus 12 and often end with the tip in the stomach 14 (although certain applications can extend further). Gastric tubes 100 are typically used for feeding, medication administration, or removal of contents from the stomach via aspiration, suction, or gravity drainage.

It has been estimated that around 1.2 million nasogastric tubes are inserted every year in the US. Similarly it has been estimated that 10 million nasogastric tubes are used yearly in Europe, with UK alone contributing to 1 million of those numbers. Some studies have suggested studies expect a 6.4% growth in usage by 2024. Other studies have noted that 24% of hospitalized pediatric patients in the US required temporary use of a NG/OG tube 100.

Currently, placement of gastric tubes 100 is accomplished, for a nasogastric tube 100 implementation, by using the nostril with the largest opening to insert the nasogastric tube 100 down the back of the nostril to the nasopharynx. The medical professional will generally ask the patient 10 to swallow once the tube 100 enters the nasopharynx. If the patient 10 is not able to mimic the swallowing action, the caregiver will often ask the patient 10 to sip water. For oro-gastric tubes 100 the technique is similar although placement starts in the oral cavity.

Complications that result from improper OG/NG tube 100 placement including pneumothorax, pulmonary hemorrhage, pleural effusion, empyema, trauma injuries, abscess formation, nose bleeds, asphyxia, secondary infections, pneumonitis, and development of tracheal-esophageal fistula. Other complications that can occur from improper tube 100 placement include tube migration, perforation of the tube 100, and the tube obstruction.

The ability to safely assess gastric tube 100 placement is a key skill that most medical professionals are required to learn. It is essential that the medical professional apply a systematic approach to such assessments as incorrect gastric tube 100 placement can result in life threatening complications. Historically, nurses or other qualified healthcare professionals can verify the placement of the OG/NG tube 100 by performing two of the following methods: asking the patient to hum or talk (wherein coughing or choking means the tube 100 is properly placed); use an irrigation syringe to aspire gastric contents; chest xray, lower the open end or proximal of the OG/NG tube 100 into a cup of water (bubbles indicate that the tube 100 is in place); or place a stethoscope over the patient's epigastrium while a 30 cc/m/ bolus using an irrigation syringe (the air enters the stomach 14 when a whooshing sound is heard).

Methods that are most commonly used for confirming or verifying gastric tube 100 placement include: measuring the pH of aspirate using pH indicator strips or radiography (e.g. chest x-ray). Although other methods are discussed, currently these are the two modalities that are the most readily accepted. In the PH testing verification methodology, after a gastric tube 100 has been inserted, it is common practice to attempt to obtain an aspirate which then can have its pH checked. The idea is that gastric contents normally have a low pH (1.5-3.5) and therefore any aspirate that has a pH this low is likely to be located in the stomach 14 and unlikely to be located elsewhere (e.g. the respiratory tract). Aspiration and PH checking can therefore potentially be used as a method of confirming safe nasogastric placement without the additional need of chest X Ray if the pH is within a safe range (0-5.5). Local guidelines, however, can differ in terms of the acceptable pH range for confirming gastric tube 100 placement and some hospitals may require chest X-Rays for all patients 10, regardless of pH aspirate. Further hindering the PH testing method is that stomach pH can be altered by medications (e.g. proton pump inhibitors) and by the frequency of feeds.

There remains a need for an accurate, efficient and cost-effective method for proper placement confirmation or verification of gastric tubes 100.

SUMMARY OF THE INVENTION

One aspect of this invention is directed to A butyric acid detection based platform for verifying placement of a patient airway device or a gastric tube comprising at least one of i) a colorimetric based butyric acid detection platform, ii) a bioelectronic sensors based butyric acid detection platform using olfactory receptors, and iii) an IR based butyric acid detection platform, wherein each platform comprises a housing configured to be coupled to the patient airway device or a gastric tube whereby flow from the coupled patient airway device or a gastric tube can flow through an internal passage of the housing; and wherein each platform comprises sensors within the housing and configured to come into contact with the flow from the coupled patient airway device or a gastric tube, the sensors including at least one of a chemical sensor array including at least one of i) colorimetric based butyric acid sensor, ii) a bioelectronic butyric acid detection sensor using olfactory receptors, and iii) an IR based butyric acid sensor.

The term integrated within the meaning of the present invention defines that the system is found in a single unit, namely mounted within a single housing.

The term "multimodal" within the meaning of the specification referencing sensors indicates that the sensor, as a whole, is directed to measuring or detecting distinct parameters.

The phrase "multimodal colorimetric based" within the meaning of the specification references a plurality of distinct color changing based sensors, wherein the distinct sensors are directed to measuring or detecting distinct parameters.

One aspect of this invention is directed to an integrated multimodal colorimetric based aspiration detection system for a respiratory device including a housing configured to be coupled to the respiratory device whereby patient exhalation can flow through an internal passage of the housing; and colorimetric based sensors within the housing and configured to come into contact with the patient exhalation, where the colorimetric based sensors are visible from the exterior of the housing, and wherein the colorimetric sensors includes at least two of i) a CO2 sensor, ii) a sensor for a first gastric acid, iii) a sensor for a second gastric acid different from the first gastric acid, and iv) a PH sensor.

One aspect of this invention is directed to a colorimetric based aspiration detection system for a respiratory device comprising a housing configured to be coupled to the respiratory device whereby patient exhalation can flow through an internal passage of the housing, and at least one colorimetric based sensors within the housing and configured to come into contact with the patient exhalation, where each of the colorimetric based sensors are visible from the exterior of the housing, and wherein the colorimetric sensors includes at least a colorimetric sensor which senses butyric acid.

One aspect of the present invention provides a method of aspiration detection and intubation placement verification for an endotracheal tube comprising the steps of: Attempting to intubate the patient with an endotracheal tube; Providing an integrated multimodal colorimetric based aspiration detection and intubation placement verification system for an endotracheal tube having a housing and colorimetric based sensors within the housing, wherein the colorimetric sensors includes a CO2 sensor and at least one of i) a sensor for a first gastric acid, ii) a sensor for a second gastric acid different from the first gastric acid, and iii) a PH sensor; Coupling the housing to the endotracheal tube whereby patient exhalation can flow through an internal passage of the housing, wherein the colorimetric based sensors within the housing come into contact with the patient exhalation; and Visualizing the colorimetric based sensors from the exterior of the housing after they have come into contact with patient exhalation to detect aspiration and to verify intubation placement.

One aspect of the invention provides a method of aspiration detection and intubation placement verification for an endotracheal tube comprises: Attempting to intubate the patient with an endotracheal tube; Providing a multimodal aspiration detection and intubation placement verification system for an endotracheal tube having a housing and sensors within the housing, wherein the sensors include at least i) a sensor for a first gastric acid, and ii) a sensor for a second gastric acid different from the first gastric acid; Coupling the housing to the endotracheal tube whereby patient exhalation can flow through an internal passage of the housing, wherein the sensors within the housing come into contact with the patient exhalation; and Utilizing the sensor output for at least one of Detecting aspiration and to verification of intubation placement. The sensors include an electric chemical sensor array which can detect odor molecules at concentrations of less than 10 parts per billion in the gas phase.

One aspect of the invention provides an integrated multimodal aspiration detection system for a patient airway device comprising: A housing configured to be coupled to the endotracheal tube whereby patient exhalation can flow through an internal passage of the housing; sensors within the housing and configured to come into contact with the patient exhalation, the sensors including a chemical sensor array including at least one of i) a sensor for a first gastric acid, and ii) a sensor for a second gastric acid different from the first gastric acid.

One aspect of the invention provides an integrated multimodal bioelectronics based aspiration detection system for a respiratory device comprising: A housing configured to be coupled to the respiratory device whereby patient exhalation can flow through an internal passage of the housing; Bioelectric based sensors within the housing and configured to come into contact with the patient exhalation, where the bioelectric based sensors include includes an electric chemical sensor array with at least i) a sensor for a first gastric acid, and ii) a sensor for a second gastric acid different from the first gastric acid.

One aspect of the invention provides a method of gastric tube placement verification comprising the steps of: Inserting a gastric tube within the patient; Providing a colorimetric based gastric tube placement verification system for a patient gastric tube including i) a housing configured to be coupled to the gastric tube whereby stomach content aspirate can flow through an internal passage of the housing; and ii) at least one colorimetric based sensor within the housing and configured to come into contact with the patient stomach content aspirate, the least one colorimetric based sensor configures to detect a first gastric acid; Coupling the housing of the colorimetric based gastric tube placement verification system to a proximal end of the gastric tube; Aspirating stomach content of the patient whereby stomach aspirate can flow through an internal passage of the housing; and Visually inspecting at least one colorimetric based sensor within the housing for verification of proper gastric tube placement.

One aspect of the invention provides a colorimetric based gastric tube placement verification system for a patient gastric tube comprising: a housing configured to be coupled to the gastric whereby stomach content aspirate can flow through an internal passage of the housing; and at least one colorimetric based sensor within the housing and configured to come into contact with the patient stomach content aspirate, the least one colorimetric based sensor configures to detect a first gastric acid.

One aspect of the invention provides a colorimetric based gastric tube placement verification system for a patient gastric tube comprising: a housing configured to be coupled to the gastric whereby stomach content aspirate can flow through an internal passage of the housing; and a colorimetric sensor array comprising at least two colorimetric based sensors within the housing and configured to come into contact with the patient stomach content aspirate, including i) a sensor for a first gastric acid, and ii) a sensor for a second gastric acid different from the first gastric acid.

The features that characterize the present invention are pointed out with particularity in the claims which are part of this disclosure. These and other features of the invention, its operating advantages and the specific objects obtained by its use will be more fully understood from the following detailed description in connection with the attached figures.

BRIEF DESCRIPTION OF THE FIGURES

FIG. 1A is a schematic sectional view of a subject illustrating swallowing;

FIG. 1B is a schematic sectional view of a subject illustrating aspiration;

FIG. 1C is a schematic view of a conventional gastric tube, namely a nasogastric tube, as known in the art;

FIG. 4A is a perspective view of a colorimetric based gastric tube placement verification system according to another embodiment of the present invention;

FIG. 4B is an exploded perspective view of the colorimetric based gastric tube placement verification system of FIG. 4A;

FIG. 5A is a perspective view of a colorimetric based gastric tube placement verification system according to another embodiment of the present invention; and FIG. 5B is an exploded perspective view of the colorimetric based gastric tube placement verification system of FIG. 5A.

DESCRIPTION OF THE PREFERRED EMBODIMENTS

Figure 2A:
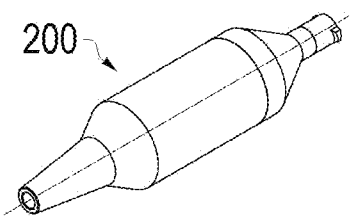
FIG. 2A is a perspective view of a colorimetric based respiratory or gastric tube placement verification system according to one embodiment of the present invention.
Figure 2B:
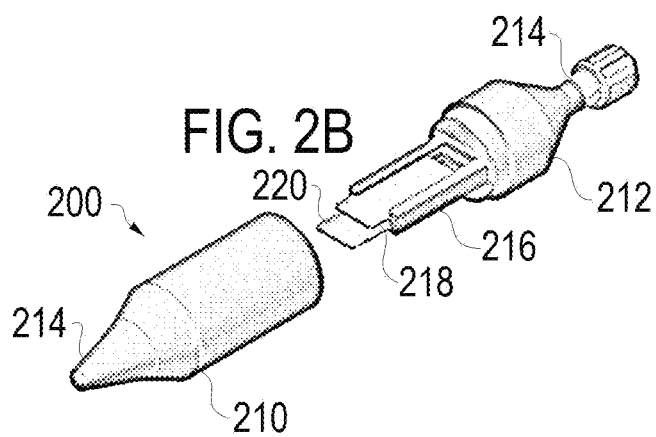
FIG. 2B is an exploded perspective view of the colorimetric based respiratory or gastric tube placement verification system of FIG. 2A.
Figure 2C:
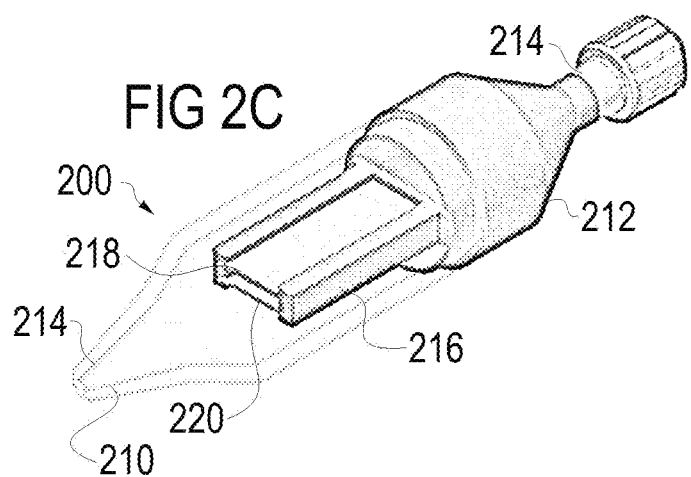
FIG. 2C is a perspective view of the colorimetric based respiratory or gastric tube placement verification system of FIG. 2A with a lower housing shown in phantom for clarity.
Figure 2D:
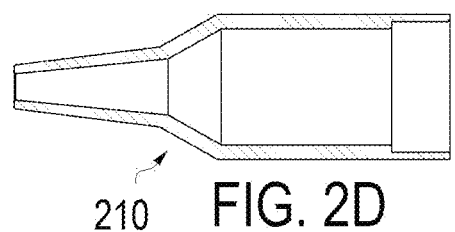
FIG. 2D is an elevation section view of the lower housing of the colorimetric based respiratory or gastric tube placement verification system of FIG. 2A.
Figure 2E:
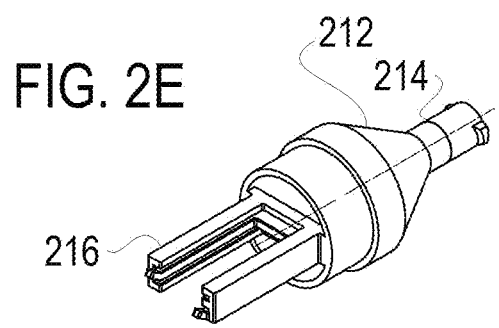
FIG. 2E is a perspective view of an upper housing of the colorimetric based respiratory or gastric tube placement verification system of FIG. 2A.
Figure 2F:
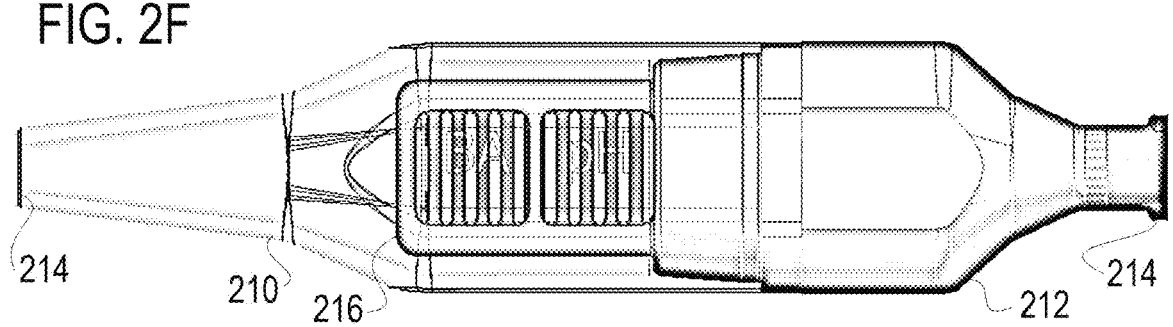
FIG. 2F is side view of an alternative colorimetric based respiratory or gastric tube placement verification system according to one embodiment of the present invention.
Figure 2G:
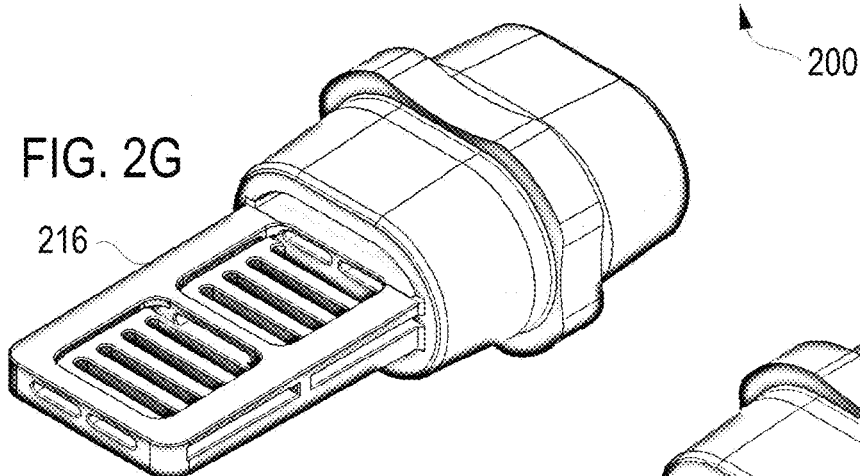
FIG. 2G is a perspective view of an intermediate colorimetric sensor holding component of the colorimetric based respiratory or gastric tube placement verification system of FIG. 2F.
Figure 2I:
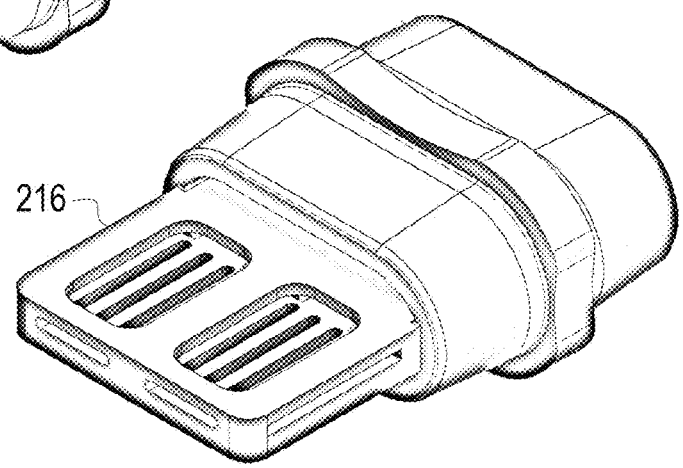
FIG. 2I is a perspective view of an intermediate colorimetric sensor holding component of the colorimetric based respiratory or gastric tube placement verification system of FIG. 2H.
Figure 2H:
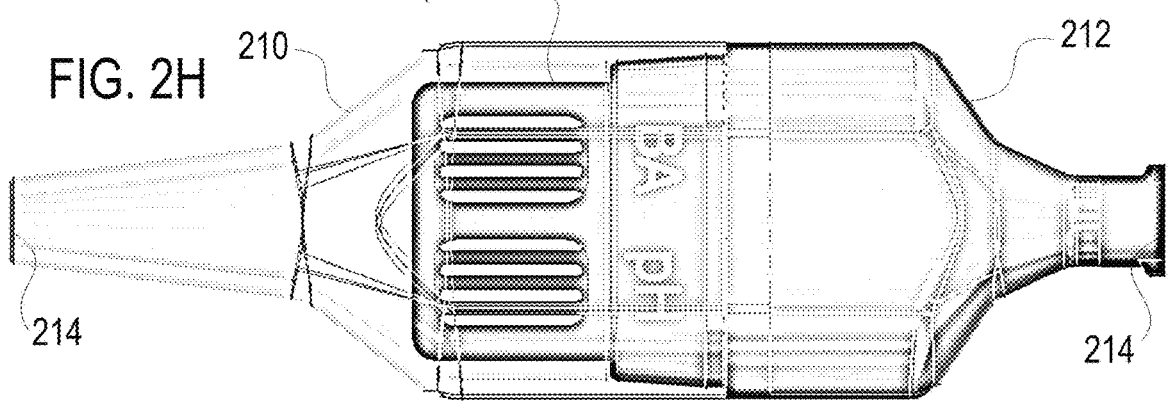
FIG. 2H is side view of an alternative colorimetric based respiratory or gastric tube placement verification system according to one embodiment of the present invention.
Figure 3A:
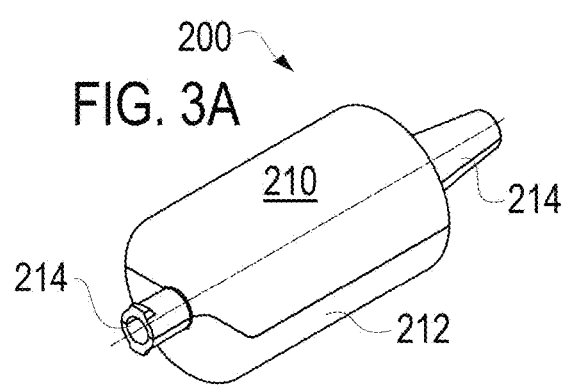
FIG. 3A is a perspective view of a colorimetric based colorimetric based respiratory or gastric tube placement verification system according to another embodiment of the present invention.
Figure 3B:
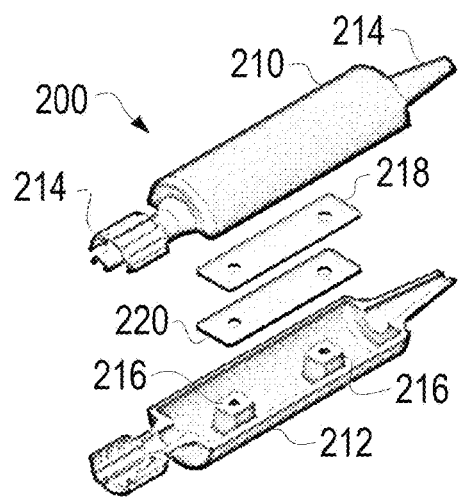
FIG. 3B is an exploded perspective view of the colorimetric based respiratory or gastric tube placement verification system of FIG. 3A.
Figure 3C:
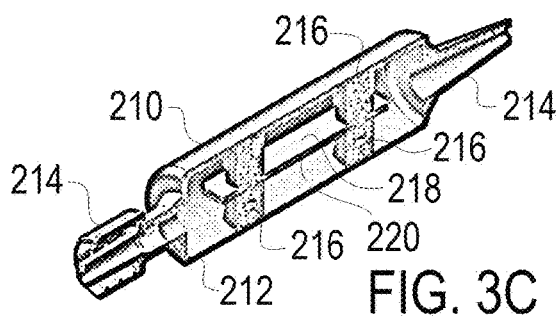
FIG. 3C is a perspective section view of the colorimetric based respiratory or gastric tube placement verification system of FIG. 3A.
Figure 3D:
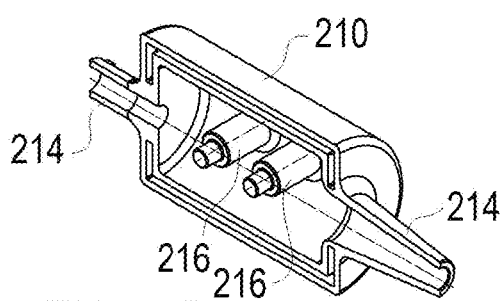
FIG. 3D is a perspective view of an upper housing of the colorimetric based respiratory or gastric tube placement verification system of FIG. 3A.
Figure 3E:
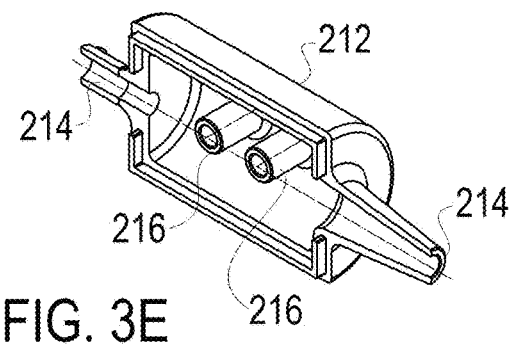
FIG. 3E is a perspective view of a lower housing of the colorimetric based respiratory or gastric tube placement verification system of FIG. 3A.

One aspect of this invention is directed to an integrated butyric and HCL acid colorimetric based detection system or platform 200, 300, which would allow for a quick, effective and safe placement verification system for orogastric, nasogastric and feeding tubes collectively referenced as gastric tubes 100. The integrated butyric and HCL acid colorimetric based detection system or platform 200, 300 may also be implemented with respiratory assist devices such as an endotracheal tube or in the nasal cannula and masks of ventilation systems and also in CPAP devices and Bipap devices. Collectively the endotracheal tubes or the nasal cannula and masks of ventilation systems and also in CPAP devices and Bipap devices can be referenced collectively herein as patient airway device or respiratory tubes.

FIGS. 2A-E illustrate a colorimetric based respiratory or gastric tube placement verification system 200 according to one embodiment of the present invention, FIGS. 3A-E illustrate a colorimetric based respiratory or gastric tube placement verification system 200 according to another embodiment of the present invention, FIGS. 4A-B illustrate a syringe type colorimetric based gastric tube placement verification system 300 according to another embodiment of the present invention, and FIGS. 5A-B illustrate a syringe type colorimetric based gastric tube placement verification system 300 according to another embodiment of the present invention.

Each system 200 is used in a method of respiratory or gastric tube 100 placement verification comprising the steps of: Inserting a patient airway device or the gastric tube 100 within the patient 10 in a conventional fashion; Providing a colorimetric based respiratory or gastric tube placement verification system 200 for a patient respiratory or gastric tube 100 including i) a housing 210, 212 configured to be coupled to the patient airway device or the gastric tube 100 whereby the tube aspirate such as stomach 14 content aspirate can flow through an internal passage of the housing 210, 212; and ii) at least one colorimetric based sensor 218, 220, within the housing 210, 212, and configured to come into contact with the tube content aspirate, the least one colorimetric based sensor 218, 220 configures to detect HCL or Butyric Acid, respectively; Coupling the housing of the colorimetric based patient airway device or gastric tube placement verification system 200 to a proximal end of the patient airway device or gastric tube 100; Aspirating tube contents, such as stomach 14 content of the patient 10, whereby the tube aspirate can flow through an internal passage of the housing 210, 212; and Visually inspecting at least one colorimetric based sensor 218, 220 within the housing 210, 212 for verification of proper patient airway device or gastric tube 100 placement.

HCl, Hydrochloric acid or muriatic acid, is a primary acid found in the stomach and in stomach aspirate. Hydrochloric acid or muriatic acid is a colorless inorganic chemical system with the formula HCl. Hydrochloric acid has a distinctive pungent smell. It is classified as a strongly acidic acid and can attack the skin over a wide composition range, since hydrogen chloride completely disassociates in aqueous solution. Hydrochloric acid is the simplest chlorine-based acid system. It is the solution of hydrogen chloride and water in a variety of other chemical species including hydronium and chloride ions. It is a naturally occurring component of the gastric acid produced in the digestive system of most animal species, including humans.

Butyric acid, also known under the systematic name butanoic acid is a carboxylic acid with the structural formula $CH_3CH_2CH_2CO_2H$. Classified as a carboxylic acid, it is oily, colorless liquid that is soluble in water, ethanol, and ether. Isobutyric acid is an isomer. Butyric acid is a carboxylic acid found in rancid butter, parmesan cheese, and vomit, and has an unpleasant odor and acrid taste, with a sweetish aftertaste (similar to ether). Butyric acid is a fatty acid occurring in the form of esters in animal fats and plant oils.

As noted above, FIGS. 2A-E illustrate a colorimetric based patient airway device or gastric tube 100 placement verification system 200 according to one embodiment of the present invention, with FIGS. 2F-I showing two alternative embodiments. The housing 210 and 212 is formed of transparent plastic and is formed of an upper housing 210 and a lower housing 212 that can be glued together. The housing defines an internal passage there through with couplings 214 on the housing 210 and 212 to couple to the proximal end of the tube 100 and other components upstream thereof, like a suction pump. The connections or coupling 214 may be a luer lock attachment or other conventional attachment components common in the medical fields.

The upper housing 210 includes sensor supports 216 in the form or slots receiving two colorimetric sensors 218 and 220 therein detecting HCL and Butyric Acid, respectively. In the embodiments of FIGS. 2F-2I the supports 216 are formed in a separate modeled element or housing that is press fit into the housing 210. The colorimetric sensors 218 and 220 form an optical chemical sensor array and each are formed as a substrate, generally filter paper, impregnated with an indicator that visibly changes color via a chemical reaction in the presence of a present amount of the sensed target substrate. See for example Johnson Test Paper, CBRNE Tech Index (http://www.cbrnetechindex.com/Chemical-Detection/Technology-CD/Colorimetric-CD-T), and Millipore Sigma.

For the purpose of the present invention the colorimetric sensors 218 and 220 will exhibit a color change generally in less than 2 seconds when exposed to the parameter of interest. For example, the colorimetric paper from Johnson Test paper forming the HCL sensor 218 changes color from blue to pink in the presence of HCl, with the sensitivity of the paper specified to be 0.5 ppm. The test or filter paper forming the Butyric Acid sensor 220 changes color in the presence of Butyric Acid, with the sensitivity of the paper specified to be 0.5 ppm. The sensor 220 should has a base color and a triggered color different from the sensor 218.

As noted above, FIGS. 3A-E illustrate a colorimetric based the patient airway device or the gastric tube 100 placement verification system 200 according to another embodiment of the present invention. Analogous to the embodiment of FIGS. 2A-E, the housing 210 and 212 of the embodiment of FIGS. 3A-E is formed of transparent plastic and is formed of an upper housing 210 and a lower housing 212 that can be glued together. The housing defines an internal passage there through, with couplings 214 on the housing 210 and 212 to couple to the proximal end of the tube 100 and other components upstream thereof, like a suction pump. The connections or coupling 214 may be a luer lock attachment or other conventional attachment components common in the medical fields.

The upper housing includes sensor supports 216 which here are in the form of posts, again, receiving two colorimetric sensors 218 and 220 therein detecting HCL and Butyric Acid, respectively. The sensors 218 and 220 in FIGS. 3A-E are the same as used in the embodiment of FIGS. 2A-E except they are sized to be received on the posts 26 with matching holes.

In summary, the system 200 of FIGS. 2A-I uses a clear housing 210, 212 with the colorimetric paper of sensors 218 and 220 attached onto/into two slots or other holding elements formed by sensor holder 216 that will allow for aspirate to pass over the colorimetric paper sensors 218 and 220 when suction is applied via syringe or mechanical suction. The clear housing 210 and 212 allows for quick visual confirmation of any color changes in the colorimetric paper of sensors 218 and 220 to verify proper placement of the gastric tube 100 or patient airway device. It will be apparent that the illustration of proper placement of the gastric tube 100 will be via a visual change in the paper indicating the presence of gastric acids, while illustration of proper placement of the patient airway device will be via a lack of any visual change in the paper indicating the lack of a presence of gastric acids. In the patient airway devices after they are properly placed the platform 200 can act as a aspiration detector as the sensors will change color in the presence of stomach aspirate.

Similarly, the system 200 of FIGS. 3A-E uses a clear housing 210, 212 for easy visual detection/confirmation of color change of either or both of the included colorimetric paper sensors 220 and 218 (i.e. butyric acid and HCl).

The HCL sensor 218 and the butyric acid sensor 220 in the embodiments of FIGS. 2A-I and 3A-E above operate on different parameters to achieve the same purpose. In practice it is expected that there will be some situations in which the HCL sensor 218 operates faster at detecting stomach acids than the butyric acid sensor 220, and vice versa. The faster detection of one gastric acid over the other may have population dependent parameters, however including both within the system 220 improves response times as well as system efficacy. In general, the butyric acid sensor 220 may be preferable.

It is possible to add a third colorimetric sensor in the form of a PH colorimetric sensor which will effectively respond to the low PH of gastric acids. Adding a third sensor requires placement in a location that is visible through the housing 210 and 212. The normal pH range for stomach acid is between 1.5 and 3.5. The trigger point of the PH sensor may be selected within a range of intra-gastric PH ranges for humans. See pH dependence of acid secretion and gastrin release in normal and ulcer subjects. Walsh Richardson C T, Fordtran J S *J Clin Invest.* 1975 March; 55(3).462-8, One class of PH colorimetric sensor 20 is a graphene oxide based sensor that exhibits distinctive color response. See "Efficient Colorimetric pH Sensor Based on Responsive Polymer-Quantum Dot Integrated Graphene Oxide", Kwanyeol Paek, Hyunseung Yang, Junhyuk Lee, Junwoo Park, and Bumjoon J. Kim *ACS Nano* 2014 8 (3), 2848-2856 DOI: 10.1021/nn406657b. As noted above the PH of the stomach 14 of the patient 10 can change such that the PH sensor should only supplement the remaining colorimetric sensor. Further the color of the PH sensor, if present, should differ from that of the sensors 218 ad 220.

FIGS. 4A-B illustrate a syringe type colorimetric based gastric tube placement verification system 300 according to another embodiment of the present invention. The housing 310 is formed of transparent plastic and is formed as a syringe barrel of an aspirational syringe. The housing can be considered to include the plunger 312 of the syringe housing 310. The syringe barrel housing 310 includes a coupling 314 to couple to the proximal end of the tube 100 for aspiration by withdrawal of the plunger 312 in conventional fashion. The housing 310 receives two colorimetric sensors 318 and 320 therein detecting HCL and Butyric Acid, respectively. The colorimetric sensors 318 and 320 form an optical chemical sensor array combined in the form of an annular disc. Each sensor 318 and 320 are each formed analogous to sensors 218 and 220, namely as a substrate, generally filter paper, impregnated with an indicator that visibly changes color via a chemical reaction in the presence of a present amount of the sensed target substrate. The optical chemical sensor array can be held in place with a friction fit rubber ring 316, which can avoid the use of glues that would hinder the operation of the sensors 318 and 320.

FIGS. 5A-B illustrate a syringe type colorimetric based gastric tube placement verification system 300 according to another embodiment of the present invention which is analogous to the system 300 of FIGS. 4A-B. The housing 310 is formed of transparent plastic and is formed as a syringe barrel of an aspirational syringe. The housing can be considered to include the plunger 312 of the syringe housing 310. The syringe barrel housing 310 includes a coupling 314 to couple to the proximal end of the tube 100 for aspiration by withdrawal of the plunger 312 in conventional fashion. The housing 310 receives two colorimetric sensors 318 and 320 on the end of plunger 312 therein detecting HCL and Butyric Acid, respectively. The colorimetric sensors 318 and 320 form an optical chemical sensor array combined in the form of an annular disc. In this embodiment the sensors 318 and 320 may be secured onto the plunger 312 with a mechanical fastener 316 (e.g. screw or bolt) to minimize the use of glue.

The system 300 of FIGS. 4A-B and 5A-B utilize the aspiration syringe of housing 310 and plunger 312 (or upper and lower housing 310 and 312) to draw aspirant through the gastric tube 100, allowing for contact of the fluid aspirant with the colorimetric paper sensors 318 and 320 in the syringe or housing 310.

As noted above Butyric acid/HCl detection in system 200 or 300 can be achieved through direct contact of sensors 218, 220, 318, 320 with aspirate after connection to the proximal end of the OG/NG gastric tube 100. Attaching the detection device or system 200 or 300 to the proximal end of the OG/NG gastric tube 100 and then either attaching the opposite end to a suction device and/or a aspirating syringe, the aspirate will come in contact with the colorimetric paper sensor 218, 220, 318, 320 giving a positive color reaction when in the presence of butyric acid and or HCl.

The system 200 and 300 show several attachment sites for the colorimetric paper sensors 218, 220, 318, 320. The colorimetric paper sensors 218, 220, 318, 320 could be attached to the sides of the housing 210, 310 that will be exposed to the stomach aspirate as it is suctioned or drawn through the system 200 or 300. These housing could have colorimetric paper sensor receiving slots within the housing with perforations or small holes which allows for liquid contact with the colorimetric paper sensors. These access sites could have small access holes or vertical openings within the internal casing. Using the butyric acid/HCl colorimetric based detection system 200 or 300 for the confirmation of proper placement of gastric tubes 100, it allows for a far greater level of certainty rather than the current methods for detection of proper placement. The apparatus 200 or 300 can detect butyric acid and HCL in quantities of parts per millions with high specificity and selectivity. The apparatus 200 or 300 is configured to adapt to current orogastric/nasogastric and feeding tubes 100.

Presented herein are a few versions of butyric acid, HCl (and or pH) colorimetric sensor 218, 220, 318 and 320 designs and described operations. Note that the above descriptions are not exhaustive, and do not restrict the applicability of the approach presented here and are meant to serve as illustrations. Further embodiments of the apparatuses 200, 300 will become obvious after study of the apparatuses 200 and 300 presented herein by persons with experience in the art or area.

Regarding specifically respiratory tubes, as discussed above, a critical step in the intubation of a patient is a determination that the breathing tube or intubation tube or endotracheal tube is placed in the trachea and not in the esophagus. The hydrochloric acid (HCL) sensor 218 is for measuring HCL concentrations of select samples of the patient exhalation. HCl is the primary acid found in the stomach. Assuming the endotracheal tube has been properly placed, the HCL sensor 218 activation (or trigger) is used for detecting aspiration of the patient. When the endotracheal tube is not properly placed the HCL sensor 20 will be triggered giving an active visual indication of improper placement. A key aspect of the present invention is the provision of a butyric acid sensor 220. Butyric acid is also known under the systematic name butanoic acid and is responsible for the stench of vomit. Thus, assuming the endotracheal tube has been properly placed, the butyric acid sensor 220 is also used for detecting aspiration of the patient. When the endotracheal tube is not properly placed the butyric acid sensor 220 will be triggered giving an active visual indication of improper placement. The HCL sensor 218 and the butyric acid sensor 220 operate on different parameters to achieve the same purpose.

Returning to the embodiment of FIGS. 2-3, consider that intubation of a patient in the emergency room is often verified only by checking for lung sounds after bagging the patient with a bag-mask apparatus. This is not a fool-proof method, and if the endotracheal tube ends up in the esophagus, pumping air into the patient's stomach can lead to additional problems. Another problem frequently associated with emergent intubations is aspiration of gastric contents. This is more common in trauma patients presenting to the emergency room, than a patient being intubated electively. Often it remains undetected until the patient presents with features of pneumonia or fibrosis. Prevention of aspiration before it occurs, or treatment as soon as it is detected is crucial.

The integrated multi-modal colorimetric sensor platform 200 of the invention includes sensors 218 and 220 formed of colorimetric HCl paper and colorimetric butyric acid paper. The system 10 is to be attached to the bag-mask apparatus so that exhaled air comes in contact with it. After proper placement of the respiratory tube, should acidic vapors be present in exhaled air from regurgitation, the colorimetric HCl papers and the colorimetric butyric acid paper will change color, alerting the doctors and nurses to possible aspiration. This system pr platform 200 may be connected to the AMBU bag while ventilating patients and allows instant confirmation of correct placement of the endotracheal tube while also checking if aspiration has occurred by checking gaseous content of exhaled air. The system 200 is particularly useful in trauma patients.

Figure 6:
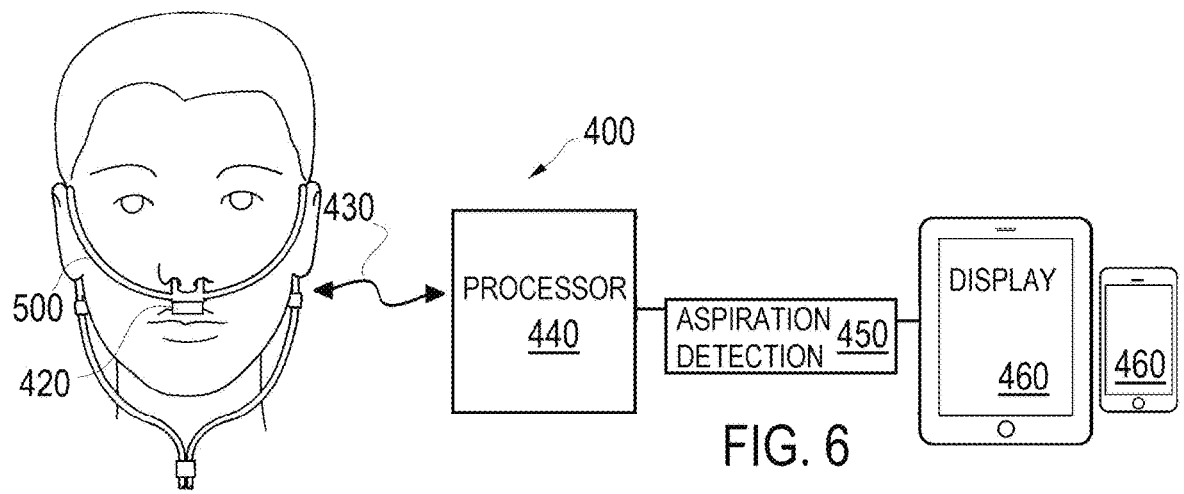
FIG. 6 is a schematic view of an integrated multimodal bioelectric based aspiration detection system for a nasal cannula according to an alternative embodiment of the present invention.
Figure 7:
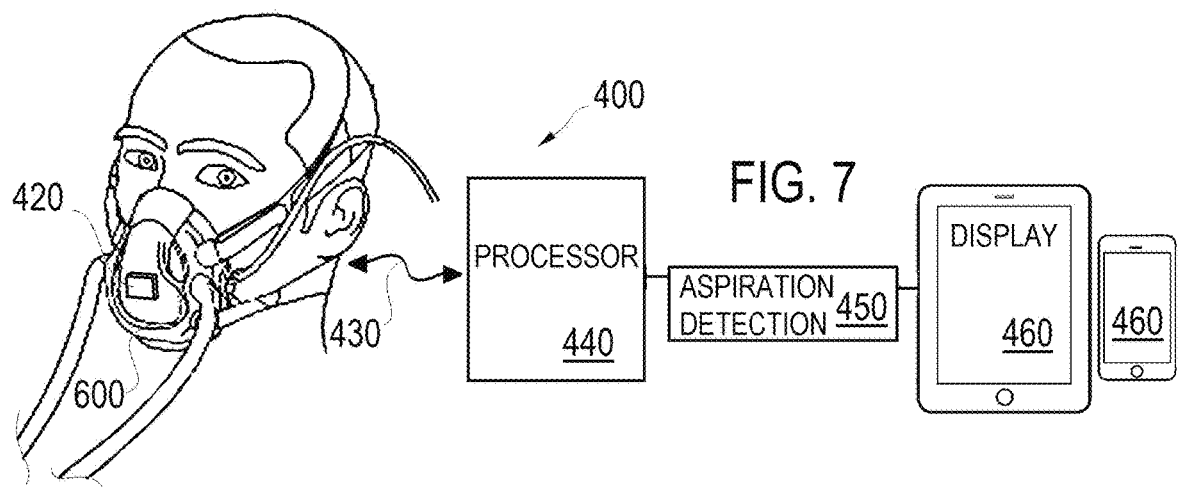
FIG. 7 is a schematic view of the integrated multimodal bioelectric based aspiration detection system of FIG. 6 implemented in a face mask according to an alternative embodiment of the present invention.
Figure 8:
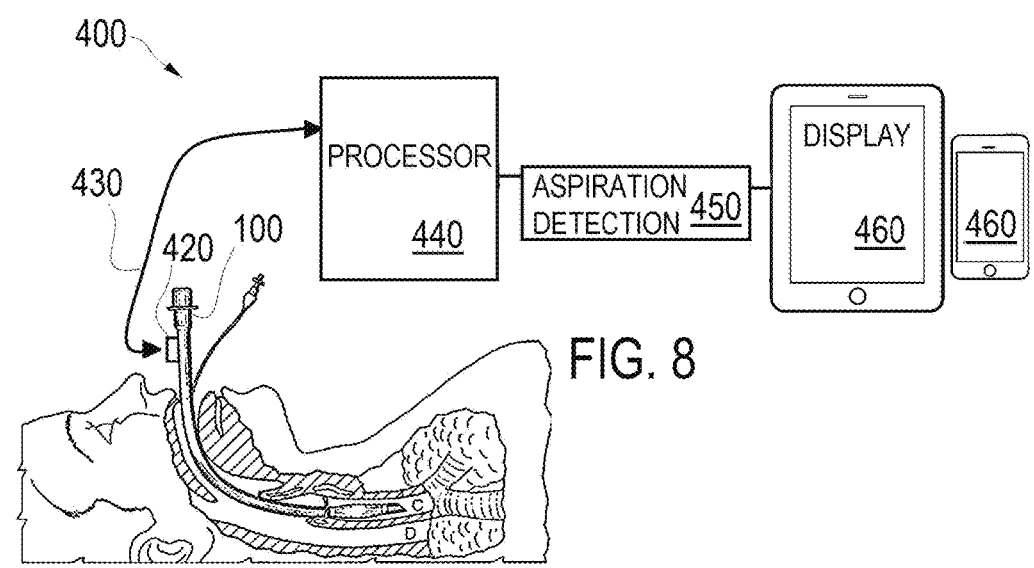
FIG. 8 is a schematic view of the integrated multimodal bioelectric based placement verification system of FIG. 6 implemented in a gastric tube according to an alternative embodiment of the present invention.

FIG. 6 is a schematic view of an integrated multimodal bioelectric based aspiration detection system or platform 400 for a nasal cannula 500 according to an alternative embodiment of the present invention. FIG. 7 is a schematic view of the integrated multimodal bioelectric based aspiration detection system or platform 400 of FIG. 6 implemented in a face mask 500 according to an alternative embodiment of the present invention. FIG. 8 is a schematic view of the integrated multimodal bioelectric based placement verification system 400 of FIG. 6 implemented in a gastric tube 100 according to an alternative embodiment of the present invention. The intubation placement verification aspects of the system 400 of FIGS. 6-8 are only relevant, of course, where the patient is intubated. The bioelectric platform 400 includes a housing for the sensors 420 configured to be coupled to the endotracheal tube 100, face mask 600 and/or nasal cannula 500 whereby tubal contents such as patient exhalation can flow through an internal passage of the housing, and bioelectronic based sensors (combining to form the sensor 420) within the housing are configured to come in contact with the patient exhalation or other tubal contents.

The bioelectronic based sensors 420 in the housing shown in FIGS. 6-8 that combine to form the multimodal sensor 20 is a chemical sensor array, specifically an electronic based chemical sensor array using olfactory receptors. The bioelectronic based sensors use olfactory receptors—proteins, which may be cloned from biological organisms, e.g., humans, that bind to specific odor molecules in emesis (as used herein emesis means stomach contents). The reactive components of the sensors react to volatile compounds on contact, such wherein the adsorption of volatile compounds on the surface of the reactive component (sometimes called the lead) causes a physical change of the reactive component, and this almost immediate response is recorded by the electronic interface transforming the signal into a digital value. The digital value from sensor 420 is transmitted over connection 430 to a processor 440. The connection 430 may be a wired connection or a wireless connection like Bluetooth® or the like. The processor 440 can review the data and detect the presence of select volatile compounds in parts per billion and the processor send aspiration detection or improper placement or proper placement signal 450 to a display 460, which may be a tablet or smartphone. The aspiration detection signal 450 may be selected when the detected levels reach above a minimal threshold and this threshold may be as low as a few parts per billion. Statistical modeling may be used to adjust the threshold to avoid minimize false positives while detecting aspirations.

The sensor 420 is multimodal for the system 400 of FIGS. 6-8 because the electronic based chemical sensor array will preferably detect at least two distinct chemicals of emesis, such as preferably HCL and butyric acid. A single chemical sensor detecting only Butyric acid is possible, but believed to be less effective than the multimodal system 400 disclosed. The multimodal electronic based chemical sensor array for the system 400 of FIGS. 6-8 is analogous to the multimodal colorimetric (or optical) based chemical sensor array for the system 200 of FIGS. 2-3 discussed above.

The system 400 of FIGS. 6-8 above can be considered to form a type of "electronic nose" as the term in known in the art. An electronic nose is an electronic sensing device intended to detect odors (or flavors). Since at least 1982, research has been conducted to develop technologies, commonly referred to as electronic noses, which could detect and recognize odors and flavors. Electronic noses traditionally include three major parts: a sample delivery system, a detection system, a computing system. Here the sample delivery system is the nasal cannula 500 of FIG. 6, the face mask 600 of FIG. 7 and the gastric tube 100 of FIG. 8 coupled with the attached housing of the sensor array. The detection system is the reactive components of the sensor 420, while the computing system is the processor 440 (although a display 460 is often deemed important to show results).

The integrated multimodal bioelectric based aspiration detection and placement verification system 400 of FIGS. 6-8 can be easily integrated with the integrated multimodal colorimetric based aspiration detection and placement verification system 200 of FIGS. 2-3 simply by incorporating the housing holding the bioelectronic based sensors 420 of the system 400 of FIGS. 6-8 with the housing 210 or 212 of integrated multimodal colorimetric based aspiration detection and placement verification system 200 of FIGS. 2-3. The merged embodiments would operate independently and yield electronic (display 460) and visual (colorimetric) indication of aspiration detection and proper gastric or respiratory placement.

Early detection and/or prevention of aspiration of emesis or other chemical/organic compounds via bioelectronic analysis of volatile organic compounds (VOCs) including butyric acid can decrease mortality and morbidity. Detecting exhaled or passively released VOCs (including butyric acid and/or other compounds readily found in emesis) facilitates timely early interventions, such as establishing airway protection (intubation), suctioning, pharmacological intervention (opiate and/or benzodiazepine reversal), elevating the head of the bed, and/or improving the level of consciousness, etc.

As shown in FIGS. 6-8, bioelectronic analysis can be adapted to a variety of platforms, such as: endotracheal tubes, facemasks, nasal cannulas, CPAP machines, etc. The bioelectronic analyzer can be a portable unit or adapted to preexisting modules (e.g., the display 460 can be via a downloadable app on a user's handheld device). The bioelectronic analyzer will use variations in baseline detection of products of emesis and/or precursors of aspirant and may give visual data on the display via numeric valves and/or positive indication, as well as a possible audible warning when predetermined thresholds are met. These alarm mechanisms/warnings can be transmitted via Bluetooth, Wi-fi or direct connection to a display on a hand held device or to a dedicated module with visual display. Predictive algorithms would be used from compiled data to establish patterns and protocols, followed by standardized interventions which would be initiated after positive detection of emesis or a precursor of emesis.

The effective "bioelectronic nose" of the integrated multimodal bioelectric based aspiration detection and placement verification system 400 can detect odor molecules at extremely low concentrations of less than 10 parts per billion in the gas phase and less than 10 parts per million in liquid phase. The apparatus 400 is configured to discriminate the smells of emesis, preemptively avoiding aspiration or detecting aspiration earlier in the process. In short, binding the odorants of interest to the olfactory receptors of the bioelectronic nose electronic chemical array, the odorant products of emesis are timely recognized and an audiovisual alarm may be effectively and timely triggered.

Presented above are a few versions of the bioelectronic analyzer designs and described operations. Note that the preceding descriptions are not exhaustive, and do not restrict the applicability of the approach presented here and are meant to serve as illustrations. Further embodiments of the apparatuses will become obvious after study of the apparatuses presented here by persons with experience in the art or area.

Figure 9:
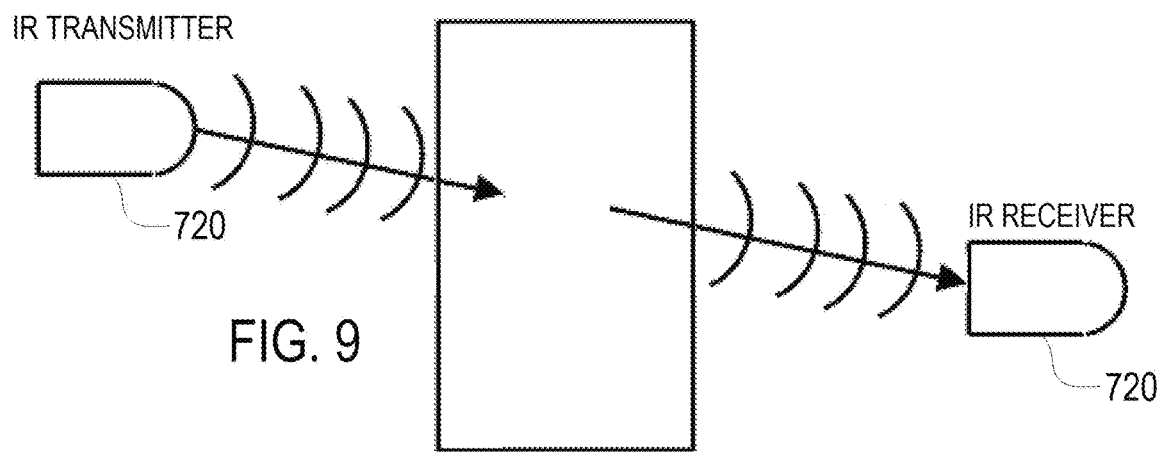
FIG. 9 is a schematic view of a transmittance IR based butyric acid detection sensor for use in an IR based butyric acid detection platform according to the present invention.
Figure 10:
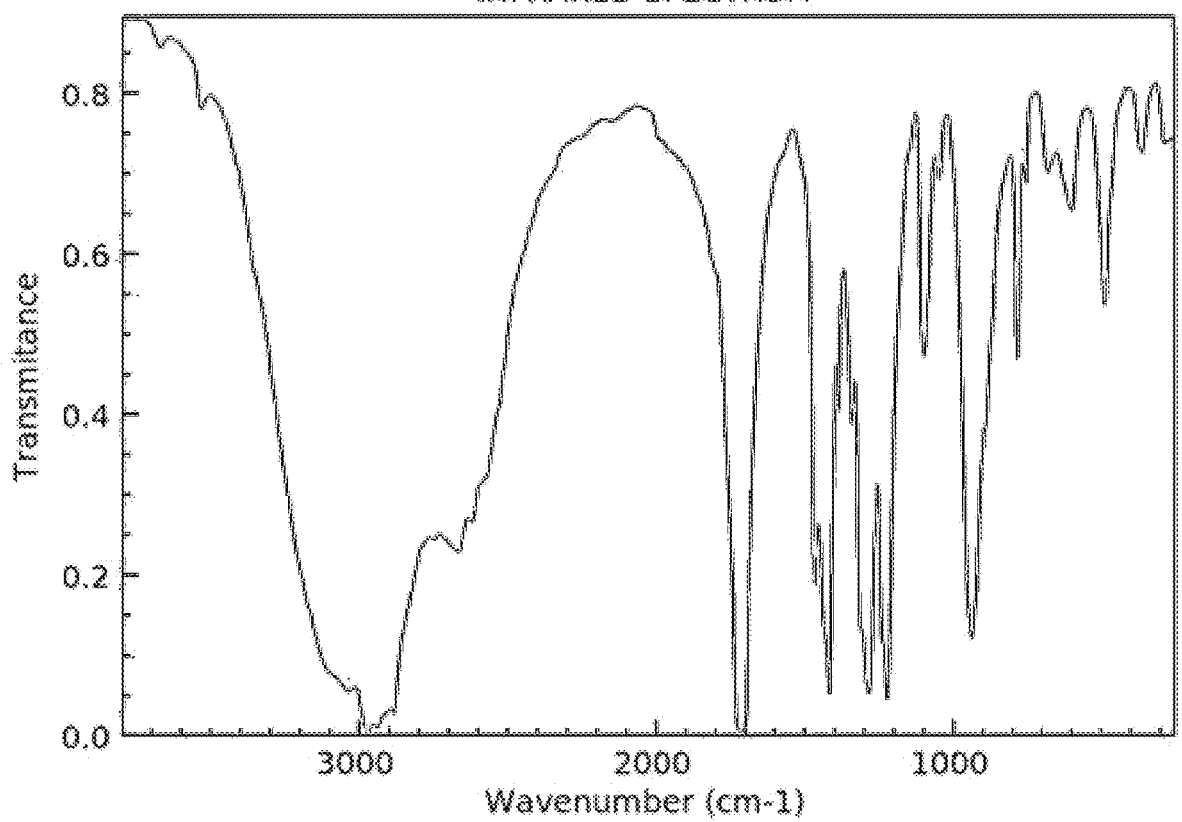
FIG. 10 is a schematic view of a transmittance or absorption IR spectrum of butyric acid for understanding an IR based butyric acid detection platform according to the present invention.

FIG. 9 is a schematic view of a transmittance IR based butyric acid detection sensor 720 for use in an IR based butyric acid detection platform 700 according to the present invention. Essentially an IR transmitter directs light of a select wavelength to the subject of interest. In a transmittance type system the receiver will receive the light not absorbed by the subject of interest. In a reflectance type system the system is based upon the amount of light reflected from the substrate of interest, but the general operational principles are the same. FIG. 10 is a schematic view of a transmittance or absorption IR spectrum of butyric acid for understanding an IR based butyric acid detection platform according to the present invention. As shown in FIG. 10 butyric acid has two wavelengths in which there is exhibited substantial absorbance, resulting is significant sensitivity of the sensor 700 when selecting or operating at these wavelengths. Operationally the platform 700 detects the amount of butyric acid, if any, similar to photoplysmosmographic sensors detect blood oxygenation.

Figure 11:
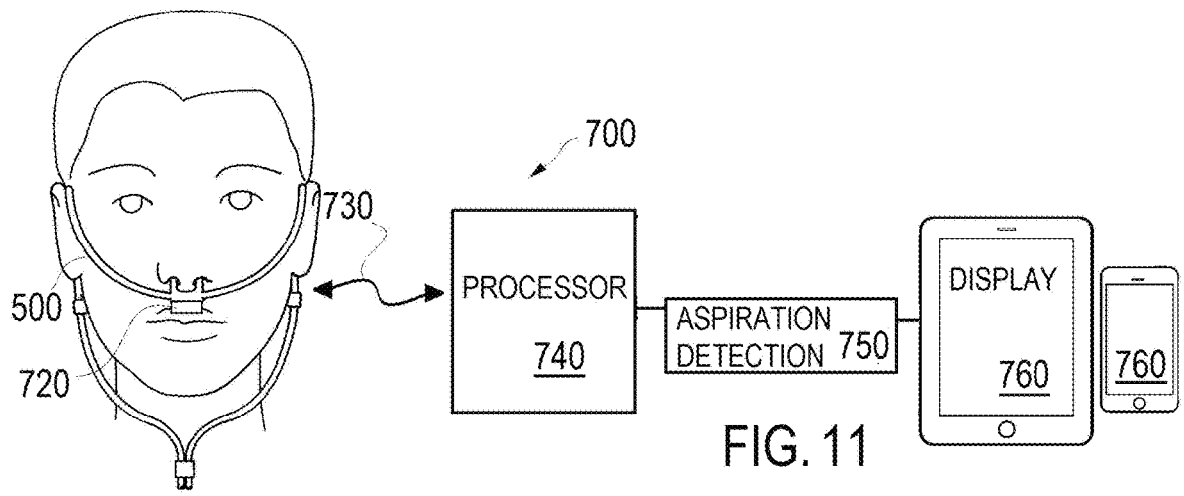
FIG. 11 is a schematic view of an IR based butyric acid detection platform for a nasal cannula according to an alternative embodiment of the present invention.
Figure 12:
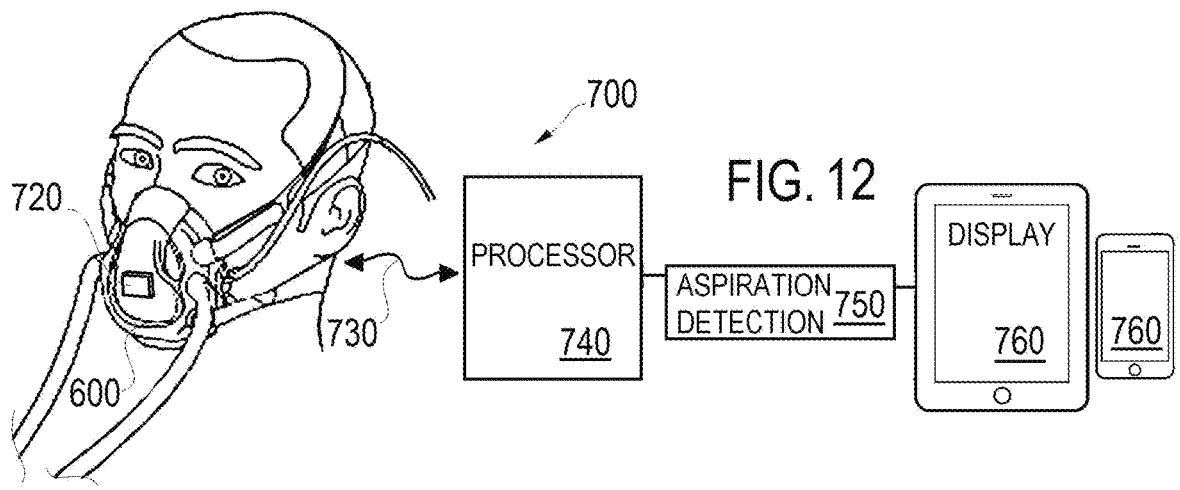
FIG. 12 is a schematic view of the IR based butyric acid detection platform of FIG. 6 implemented in a face mask according to an alternative embodiment of the present invention.
Figure 13:
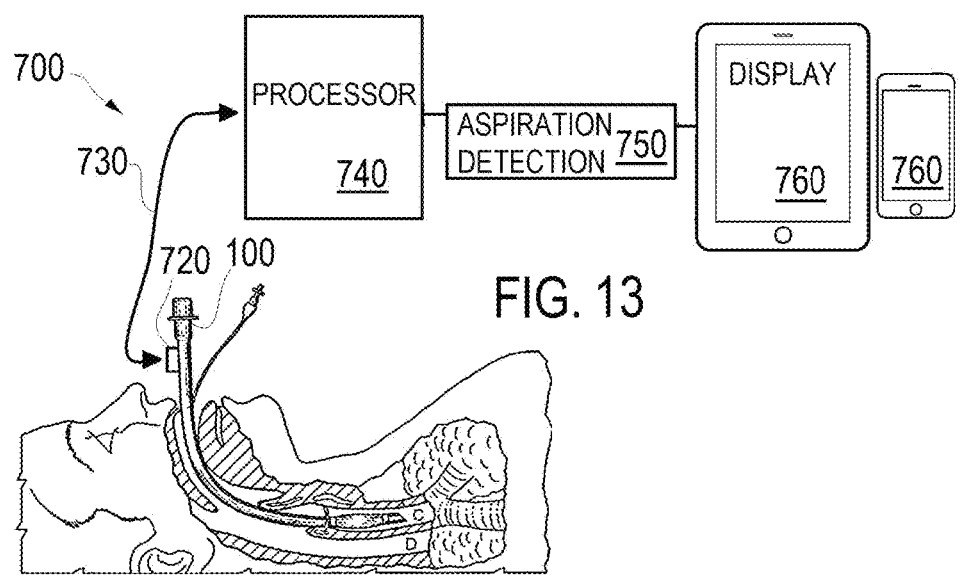
FIG. 13 is a schematic view of the IR based butyric acid detection platform of FIG. 6 implemented in a gastric tube according to an alternative embodiment of the present invention.

This principle allows the creation of an IR based butyric acid detection platform 700 as generally shown in FIGS. 11-13. FIG. 11 is a schematic view of an IR based butyric acid detection platform 700 for a nasal cannula 500 according to an alternative embodiment of the present invention; FIG. 12 is a schematic view of the IR based butyric acid detection platform 700 of FIG. 6 implemented in a face mask 600 according to an alternative embodiment of the present invention; and FIG. 13 is a schematic view of the IR based butyric acid detection platform 700 of FIG. 6 implemented in a gastric tube 100 according to an alternative embodiment of the present invention.

The IR based butyric acid detection platform 700 includes a housing for the sensors 720 configured to be coupled to the gastric or endotracheal tube 100, face mask 600 and/or nasal cannula 500 whereby tubal contents such as patient exhalation can flow through an internal passage of the housing, and bioelectronic based sensors (combining to form the sensor 720) within the housing are configured to come in contact with the patient exhalation or other tubal contents.

The IR based butyric acid sensor 720 in the housing shown in FIGS. 6-8 has a digital value which is transmitted over connection 730 to a processor 740. The connection 730 may be a wired connection or a wireless connection like Bluetooth® or the like. The processor 740 can review the data and detect the presence of butyric acid in parts per billion and the processor send aspiration detection or improper placement or proper placement signal 750 to a display 760, which may be a tablet or smartphone. The aspiration detection signal 750 may be selected when the detected levels reach above a minimal threshold and this threshold may be as low as a few parts per billion. Statistical modeling may be used to adjust the threshold to avoid minimize false positives while detecting aspirations.

While the invention has been shown in several particular embodiments it should be clear that various modifications may be made to the present invention without departing from the spirit and scope thereof. The scope of the present invention is defined by the appended claims and equivalents thereto.

What is claimed is:

1. A butyric and hydrochloric acid detection based platform for verifying placement of a patient airway device or a gastric tube comprising:
   i) a transparent plastic cylindrical housing having an internal passage there through and couplings on each end of the housing;
   ii) sensor supports coupled to the housing and extending into the internal passage;
   iii) a colorimetric based butyric acid sensor that visibly changes color via a chemical reaction in the presence of butyric acid, wherein the butyric acid sensor is mounted on the sensor supports;
   iv) a colorimetric based hydrochloric acid sensor that visibly changes color via a chemical reaction in the presence of hydrochloric acid, wherein the hydrochloric acid sensor is mounted on the sensor supports stacked with the butyric acid sensor, whereby the sensors are in the same axial position along the internal passage of the housing; and
   wherein the housing is configured to be coupled to the patient airway device or a gastric tube via the couplings whereby flow from the coupled patient airway device or a gastric tube can flow through the internal passage of the housing and around the stacked colorimetric based hydrochloric acid sensor and colorimetric based butyric acid sensor and contacting both the colorimetric based hydrochloric acid sensor and colorimetric based butyric acid sensor; and
   wherein the stacked colorimetric based hydrochloric acid and colorimetric based butyric acid sensors within the housing and which are configured to come into contact with the flow from the coupled patient airway device or a gastric tube form a chemical sensor array.

2. The butyric and hydrochloric acid detection based platform according to claim 1, wherein the platform is configured for coupling to an endotracheal tube.

3. The butyric and hydrochloric acid detection based platform according to claim 2, wherein the platform is configured as an intubation placement verification system.

4. The butyric and hydrochloric acid detection based platform according to claim 1, wherein the sensor supports coupled to the housing and extending into the internal passage are in the form of slots receiving the stacked colorimetric based hydrochloric acid and colorimetric based butyric acid sensors.

5. The butyric and hydrochloric acid detection based platform according to claim 4, wherein the platform is configured for coupling to an gastric tube.

6. The butyric and hydrochloric acid detection based platform according to claim 4, wherein the platform is configured for coupling to an endotracheal tube.

7. The butyric and hydrochloric acid detection based platform according to claim 1, wherein the sensor supports coupled to the housing and extending into the internal passage are formed as a separated molded element coupled to the housing.

8. The butyric and hydrochloric acid detection based platform according to claim 7, wherein the platform is configured for coupling to an gastric tube.

9. The butyric and hydrochloric acid detection based platform according to claim 7, wherein the platform is configured for coupling to an endotracheal tube.

* * * * *